UNITED STATES PATENT OFFICE.

ALBERT D. RICHARDS, OF SOMERVILLE, MASSACHUSETTS, ASSIGNOR, BY MESNE ASSIGNMENTS, TO GROSVENOR & RICHARDS.

IMPROVEMENT IN MEDICATED PLASTERS.

Specification forming part of Letters Patent No. 111,682, dated February 7, 1871; reissue No. 6,867, dated January 18, 1876; application filed December 14, 1875.

*To all whom it may concern:*

Be it known that I, ALBERT D. RICHARDS, of Somerville, in the county of Middlesex and State of Massachusetts, have invented an Improvement in Medicated Plasters; and I hereby declare that the following is a full, clear, and exact description of the same.

This invention relates to an improvement in medicated plasters, to be used to relieve pain, in which belladonna is the active remedial agent employed.

These plasters, as heretofore prepared, have usually been made by simply incorporating the belladonna with the material used to give adhesiveness—Burgundy pitch and resin plaster being well recognized and the usual materials employed for this purpose. The defects of such plasters are various. The compound dries up quickly and becomes stiff, when it is liable to crack off; the plaster cannot readily be applied without artificial heat; and, again, hot weather or the heat of the body will cause the compound to "run", so that the plaster will "travel" and become easily displaced. In order to remedy these defects in medicated belladonna plasters, I propose to incorporate rubber in the base or vehicle used to carry the belladonna. As the plasters have been made hitherto, it has been impossible to effect an even distribution of the belladonna through the base, but the addition of the rubber facilitates the admixture of the belladonna, and renders it possible to distribute it evenly throughout the mass. The presence of the rubber also causes the plaster to remain elastic and pliable and always ready for use, without the application of artificial heat, and, when once applied to the body, it will not only adhere firmly, but can be removed without leaving any of the compound adhering to the skin.

To enable others skilled in the art to understand and use my invention, I will proceed to describe what I consider the best mode of carrying it out.

I take two and a half ounces of Burgundy pitch, and after melting it in a suitable vessel add thereto three and a half ounces of extract of belladonna, and stir until they are thoroughly mixed and incorporated together. As soon as this compound has become cold and hard it is broken up into small pieces and mixed with eight ounces of pure rubber, cut up into pieces of suitable size. The whole is then ground in a cold state until it is reduced to a pulpy mass, in which condition it is spread onto cloth to form plasters, by means of rollers, in a well-known manner. The sheet thus formed can be rolled up and carried about, and plasters of any convenient size be cut therefrom, the nature of the compound being such that its virtue will be retained for a long time without any material deterioration.

It should be understood that the rubber could not well be used alone as a vehicle for the remedial agent, since it would not be sufficiently adhesive, hence the necessity of combining it with a material which will cause the plaster to adhere firmly. The proportions of all the above-named ingredients may be somewhat varied according to circumstances, without departing from the spirit of my invention.

What I claim as my invention, and desire to secure by Letters Patent, is—

1. A medicated plaster, composed of belladonna, pitch, and rubber, substantially as set forth.

2. A belladonna plaster in which rubber is used as an ingredient in the base or vehicle, to give elasticity and pliability, substantially as set forth.

ALBERT D. RICHARDS.

Witnesses:
JAMES PIERCE,
WILLIAM S. CHILD.